(12) United States Patent
Prakash et al.

(10) Patent No.: US 8,030,481 B2
(45) Date of Patent: Oct. 4, 2011

(54) STEVIOSIDE POLYMORPHIC AND AMORPHOUS FORMS, METHODS FOR THEIR FORMULATION, AND USES

(75) Inventors: Indra Prakash, Alpharetta, GA (US); Mani Upreti, Dunwoody, GA (US)

(73) Assignee: The Coca-Cola Company, Atlanta, GA (US)

( * ) Notice: Subject to any disclaimer, the term of this patent is extended or adjusted under 35 U.S.C. 154(b) by 97 days.

(21) Appl. No.: 11/751,625

(22) Filed: May 21, 2007

(65) Prior Publication Data

US 2008/0292764 A1    Nov. 27, 2008

(51) Int. Cl.
C07H 1/06 (2006.01)
C07H 1/08 (2006.01)
C07H 15/00 (2006.01)
C07H 17/00 (2006.01)
C07G 3/00 (2006.01)
C07G 11/00 (2006.01)

(52) U.S. Cl. ............ 536/128; 536/4.1; 536/127

(58) Field of Classification Search ............ 536/4.1, 536/127, 128
See application file for complete search history.

(56) References Cited

U.S. PATENT DOCUMENTS

| | | | |
|---|---|---|---|
| 3,723,410 A * | 3/1973 | Persinos ............... 536/18.2 |
| 4,082,858 A | 4/1978 | Morita et al. |
| 4,219,571 A | 8/1980 | Miyake |
| 4,332,830 A | 6/1982 | DuBois |
| 4,353,889 A | 10/1982 | DuBois |
| 4,361,697 A | 11/1982 | Dobberstein et al. |
| 4,381,402 A | 4/1983 | DuBois |
| 4,402,990 A | 9/1983 | DuBois |
| 4,404,367 A | 9/1983 | DuBois |
| 4,454,290 A | 6/1984 | DuBois |
| 4,590,160 A | 5/1986 | Nishihashi et al. |
| 4,599,403 A | 7/1986 | Kumar |
| 5,112,610 A | 5/1992 | Kienle |
| 5,530,106 A | 6/1996 | Navia et al. |
| PP10,562 P | 8/1998 | Sys et al. |
| PP10,563 P | 8/1998 | Brandle et al. |
| PP10,564 P | 8/1998 | Marsolais et al. |
| 5,962,678 A | 10/1999 | Payzant et al. |
| 5,972,120 A | 10/1999 | Kutowy et al. |
| 6,255,557 B1 | 7/2001 | Brandle |
| 6,331,646 B1 | 12/2001 | Schroeder et al. |
| 6,423,864 B1 | 7/2002 | Prakash et al. |
| 6,784,309 B2 | 8/2004 | Prakash et al. |
| 6,809,198 B2 | 10/2004 | El Kabbani et al. |
| 6,998,480 B2 | 2/2006 | Catani et al. |
| 7,049,435 B2 | 5/2006 | Catani et al. |
| 2002/0065245 A1 | 5/2002 | Brouwers |
| 2004/0030124 A1 | 2/2004 | Catani et al. |
| 2006/0083838 A1 | 4/2006 | Jackson et al. |
| 2006/0134292 A1 | 6/2006 | Abelyan et al. |
| 2006/0142555 A1 | 6/2006 | Jonnala et al. |
| 2007/0082102 A1 | 4/2007 | Magomet et al. |
| 2007/0082103 A1 | 4/2007 | Magomet et al. |
| 2007/0116800 A1 | 5/2007 | Prakash et al. |
| 2007/0116819 A1 | 5/2007 | Prakash et al. |
| 2007/0116820 A1 | 5/2007 | Prakash et al. |
| 2007/0116821 A1 | 5/2007 | Prakash et al. |
| 2007/0116822 A1 | 5/2007 | Prakash et al. |
| 2007/0116823 A1 | 5/2007 | Prakash et al. |
| 2007/0116824 A1 | 5/2007 | Prakash et al. |
| 2007/0116825 A1 | 5/2007 | Prakash et al. |
| 2007/0116826 A1 | 5/2007 | Prakash et al. |
| 2007/0116827 A1 | 5/2007 | Prakash et al. |
| 2007/0116828 A1 | 5/2007 | Prakash et al. |
| 2007/0116829 A1 | 5/2007 | Prakash et al. |
| 2007/0116830 A1 | 5/2007 | Prakash et al. |
| 2007/0116831 A1 | 5/2007 | Prakash et al. |
| 2007/0116832 A1 | 5/2007 | Prakash et al. |
| 2007/0116833 A1 | 5/2007 | Prakash et al. |
| 2007/0116834 A1 | 5/2007 | Prakash et al. |
| 2007/0116835 A1 | 5/2007 | Prakash et al. |
| 2007/0116836 A1 | 5/2007 | Prakash et al. |
| 2007/0116837 A1 | 5/2007 | Prakash et al. |
| 2007/0116838 A1 | 5/2007 | Prakash et al. |
| 2007/0116839 A1 | 5/2007 | Prakash et al. |
| 2007/0116840 A1 | 5/2007 | Prakash et al. |
| 2007/0116841 A1 | 5/2007 | Prakash et al. |
| 2007/0128311 A1 | 6/2007 | Prakash et al. |
| 2007/0134390 A1 | 6/2007 | Prakash et al. |
| 2007/0134391 A1 | 6/2007 | Prakash et al. |
| 2010/0137569 A1 | 6/2010 | Prakash et al. |

FOREIGN PATENT DOCUMENTS

| | | |
|---|---|---|
| CA | 2278083 | 1/2001 |
| EP | 1407679 | 4/2004 |
| JP | 52062300 | 5/1977 |
| JP | 56121453 | 9/1981 |
| JP | 56121455 | 9/1981 |
| JP | 59071662 A | 4/1984 |
| JP | 59120073 A | 7/1984 |
| JP | 60027360 A | 2/1985 |
| JP | 60037950 A | 2/1985 |
| JP | 62091161 A | 4/1985 |
| WO | 00/32621 | 6/2000 |

(Continued)

OTHER PUBLICATIONS

Mullin, J.W. (1961) Chapter 7, "Industrial Crystallization" in Crystallization, Butterworth Inc., p. 158-169.*

(Continued)

*Primary Examiner* — Shaojia Anna Jiang
*Assistant Examiner* — Scarlett Goon
(74) *Attorney, Agent, or Firm* — King & Spalding (57) ABSTRACT

Exemplary embodiments of this invention encompass a method for purifying a substantially crude stevioside, methods for preparing polymorphic and amorphous forms of stevioside, and the polymorphic and amorphous forms prepared therefrom.

11 Claims, 7 Drawing Sheets

FOREIGN PATENT DOCUMENTS

| WO | 00/52019 | 9/2000 |
|---|---|---|
| WO | WO 2006/038221 | 4/2006 |

OTHER PUBLICATIONS

Luft, J.R., Wolfley, J.R., Saik, D.I., Nagel, R.M., Lauricella, A.M., Smith, J.L., Thayer, M.H., Veatch, C.K., Snell, E.H., Malkowski, M.G., Detitta, G.T. (2007) Efficient optimization of crystallization conditions by manipulation of drop volume ratio and temperature. Protein Science, vol. 16, No. 4, p. 715-722.*

Kolář, P. Shen, J.-W., Tsuboi, A., Ishikawa, T. (2002) Solvent selection for pharmaceuticals. Fluid Phase Equilibria, vol. 194-197, p. 771-782.*

"2.2 Recrystallization" [online], [retrieved Dec. 10, 2009]. Published on the internet Sep. 12, 2003. Retrieved from the internet <http://siggy.chem.ucla.edu/VOH/136/Recrystallization.pdf>.*

Nass, K.K. (1994) Rational Solvent Selection for Cooling Crystallizations. Industrial & Engineering Chemistry Reseach, vol. 33, p. 1580-1584.*

Zell et al., Tetrahedron 56(36) 6603-16 (2000).

Shibata et al., Glucosylation of Steviol and Steviol-Glucosides in Extracts from *Stevia rebaudiana* Bertoni, Plant Physiol. 95: 152-156 (1991).

Boggan, B., "Alcohol, Chemistry, and You," online from ChemCases.Com Edition (retrieved Oct. 18, 2010), available Oct. 3, 2011.

Hancock, B.C. and Parks, M., "What is the True Solubility Advantage for Amorphous Pharmaceuticals," *Pharmaceuticals Research* vol. 17, No. 4, pp. 397-404 (2000).

Luft, J.R., et al., "Efficient optimization of crystallization conditions by manipulation of drop volume and temperature," *Protein Science* vol. 16, No. 4, pp. 715-722 (2007).

Kojima, S. "ICH Guideline for Residual Solvents (Q3C)," Proceedings of the 4$^{th}$ International Conference on Harmonization of Technical Requirements for Registration of Pharmaceuticals, online (retrieved Apr. 2, 2010), Brussels, Belgium Jul. 16-18, 1997.

Mullin, J.W., "Industrial Crystallization" in *Crystallization*, Butterworth Inc., pp. 158-169 (1961).

PTI Process Chemicals, "Denatured Alcohol MSDS," online (retrieved Oct. 18, 2010), published Apr. 25, 2005.

* cited by examiner

Figure 1. XRPD pattern comparison of stevioside 1·

STEVIOSIDE POLYMORPHIC AND AMORPHOUS FORMS, METHODS FOR THEIR FORMULATION, AND USES

FIELD OF INVENTION

This invention relates generally to polymorphic and amorphous forms of stevioside and methods for preparing polymorphic and amorphous forms of stevioside. More particularly, this invention relates to polymorphic and amorphous forms of stevioside having improved rates of dissolution.

BACKGROUND OF INVENTION

Stevioside is a high-potency diterpenoid glycoside sweetener having the chemical structure:

Stevioside

Stevioside is isolated and extracted, along with other steviol glycosides, from the *Stevia rebaudiana* (Bertoni) plant ("*Stevia*"), which is commercially cultivated in Japan, Singapore, Taiwan, Malaysia, South Korea, China, Israel, India, Brazil, Australia, and Paraguay. It is an alternative non-caloric sweetener with functional and sensory properties superior to those of many high-potency sweeteners. Processed forms of *Stevia* can be 70 to 400 times more potent than sugar. The use of stevioside, however, is made more difficult by its low water solubility of approximately 1.25 g/L at room temperature (U.S. Pat. No. 4,082,858). Accordingly, it would be desirable to develop polymorphic and amorphous forms of stevioside that have improved rates of dissolution.

U.S. Pat. No. 5,962,678 discloses the re-crystallization of stevioside using an anhydrous methanol solution to obtain an 91.6% pure stevioside. By repeating the re-crystallization with aqueous methanol numerous times, the purity of stevioside may be increased to over 99%. U.S. Patent Publication No. 2007/0082103 discloses a method for purifying stevioside by recrystallization from methanol and then with 90% ethanol, asserting a two-step recrystallization from crude stevioside (64.6%) results in the formation of >99% pure stevioside in very high yield. These prior art methods, however, do not provide a substantially pure stevioside composition using only a single recrystallization step. Accordingly, it would be desirable to develop a method of purifying stevioside using a simple and economical crystallization method.

SUMMARY OF INVENTION

Exemplary embodiments of the invention address the above-identified need by providing polymorphic and amorphous forms of stevioside and methods for making polymorphic and amorphous forms of stevioside.

Exemplary embodiments of the invention address the above-identified need by providing a substantially pure stevioside, polymorphic and amorphous forms of stevioside, methods for purifying stevioside, and methods for making polymorphic and amorphous forms of stevioside.

In a particular embodiment, the method for purifying stevioside comprises a simple crystallization. In one embodiment, a method for purifying stevioside comprises the steps of combining crude stevioside and an organic solvent or an aqueous organic solvent to form a stevioside solution, the aqueous organic solution comprising water in an amount from about 5% to about 25% by weight, and crystallizing from the crude stevioside solution, in a single step, a substantially pure stevioside in a purity greater than about 95% by weight on a dry basis.

In other particular embodiments, different polymorph and amorphous forms of stevioside and methods for preparing different polymorph and amorphous forms of stevioside are provided Other objects, features, and advantages of the invention will be apparent from the following detailed description, drawings, and claims. Unless otherwise defined, all technical and scientific terms and abbreviations used herein have the same meaning as commonly understood by one of ordinary skill in the art to which this invention pertains. Although methods and compositions similar or equivalent to those described herein can be used in the practice of the present invention, suitable methods and compositions are described without intending that any such methods and compositions limit the invention herein.

DETAILED DESCRIPTION OF INVENTION

Stevioside is a natural high-potency sweetener that generally is available at moderate cost. However, stevioside generally has a relatively low solubility which makes it difficult to incorporate into orally ingestible compositions. Embodiments of the present invention address these needs by providing polymorphic and amorphous forms of stevioside having improved rates of dissolution, and methods for making polymorphic and amorphous forms of stevioside having improved rates of dissolution.

Briefly described, exemplary embodiments of the present invention provide a method for forming polymorph and/or amorphous forms of a stevioside and the polymorph and amorphous forms produced thereby. In particular embodiments, the composition of the substantially pure stevioside comprises one, or more than one, polymorph(s) of stevioside. Still other exemplary embodiments of this invention encompass an amorphous form of stevioside and methods of preparing amorphous forms of stevioside. In yet another embodiment, a method for converting one form of polymorph into another form of polymorph or amorphous form is provided. Exemplary embodiments of this invention are described in detail below and illustrated in FIGS. 1-5.

As used herein, the term "substantially pure stevioside" refers to a stevioside composition that includes at least about 80% by weight of stevioside on a dry basis. In another aspect, the substantially or substantially pure stevioside compositions include at least about 85% by weight, at least about 90% by weight, at least about 95% by weight, or at least about 98% by weight of stevioside on a dry basis.

As used herein, "purity" represents the weight percentage of stevioside present in a stevioside composition in raw or purified form. In one embodiment, a stevioside composition comprises stevioside in a particular purity, with the remainder of the composition comprising a mixture of other steviol glycosides or any component that is not stevioside. The purity of the composition may be measured using methods known to those of ordinary skill in the art. One such method includes high performance liquid chromatography (HPLC). Those of ordinary skill in the art also should appreciate that moisture in the sample may affect the accuracy of purity measurements. Accordingly, it is particularly desirable that the composition be substantially dry. As used herein, a substantially dry composition comprises up to about 10% by weight of moisture.

As used herein, the term "substantially pure form" refers to a stevioside composition that includes at least about 80% by weight of a particular polymorphic or amorphous form of stevioside. In another aspect, the substantially pure form of a stevioside composition includes at least about 85% by weight, at least about 90% by weight, at least about 95% by weight, or at least about 98% by weight of a particular stevioside polymorphic or amorphous form.

Polymorphic and Amorphous Forms of Stevioside

It has been discovered that at least two different polymorphic forms of stevioside result from using the purification method described hereinbelow, including: Form 1: a stevioside hydrate; and Form 2: a stevioside solvate (methanol solvate 2A and ethanol solvate 2B). A third polymorphic form of stevioside, an anhydrous stevioside, also may result from the method described hereinbelow (not shown). Those of ordinary skill in the art will appreciate that both the organic solvent or aqueous organic solvent and the temperatures of the purification process described herein may influence the resulting polymorphs in a substantially pure stevioside composition.

Polymorphism is defined as the ability of a substance to exist as two or more crystalline states that have different arrangements and/or conformations of the molecules in the crystal lattice. Approximately 30% of organic compounds are believed to exhibit polymorphism (Zell, et al., *Tetrahedron* 56(36)6603-16 (2000)). Polymorphism is important in the formulation of pharmaceuticals, pigments and dyes, sweeteners, explosives, and agrochemicals. Polymorphism may cause physical properties such as density, melting point, and rate of dissolution to change.

The polymorphs of Stevioside were identified by analysis of samples with powder x-ray diffraction (XRPD), a technique well known to those skilled in the art. FIGS. 1-4 are XRPD scans of substantially pure stevioside polymorphic forms created by plotting the scattering intensity versus the scattering angle 2θ. Samples were analyzed by XRPtD using a Shimadzu XRD-6000 X-ray powder diffractometer using Cu Kα radiation. The instrument was equipped with a long fine focus X-ray tube. The tube voltage and amperage were set to 40 kV and 40 mA, respectively. The divergence and scattering slits were set at 1°, and the receiving slit was set at 0.15 mm. Diffracted radiation was detected by a NaI scintillation detector. A 0-20 continuous scan at 3°/min (0.4 sec/ 0.02° step) from 2.5 to 40° 2θ was used. A silicon standard was analyzed to check the instrument alignment. Data were collected and analyzed using XRD-60000 v. 4.1. The patterns exhibit resolution of reflections, indicating that the samples are comprised of crystalline materials.

Figure 1:
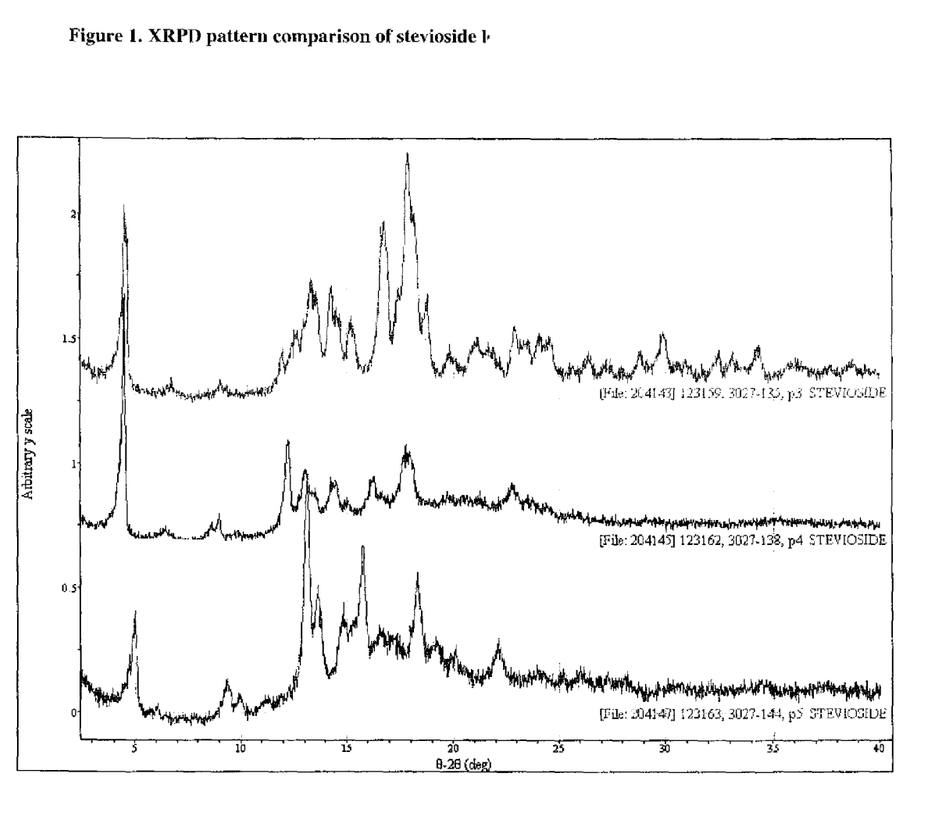
FIG. 1 is a powder x-ray diffraction scan comparing three stevioside polymorphs, Forms 1, 2A, and 2B, on a plot of the scattering intensity versus the scattering angle 2 θ in accordance with an embodiment of this invention.
Figure 2:
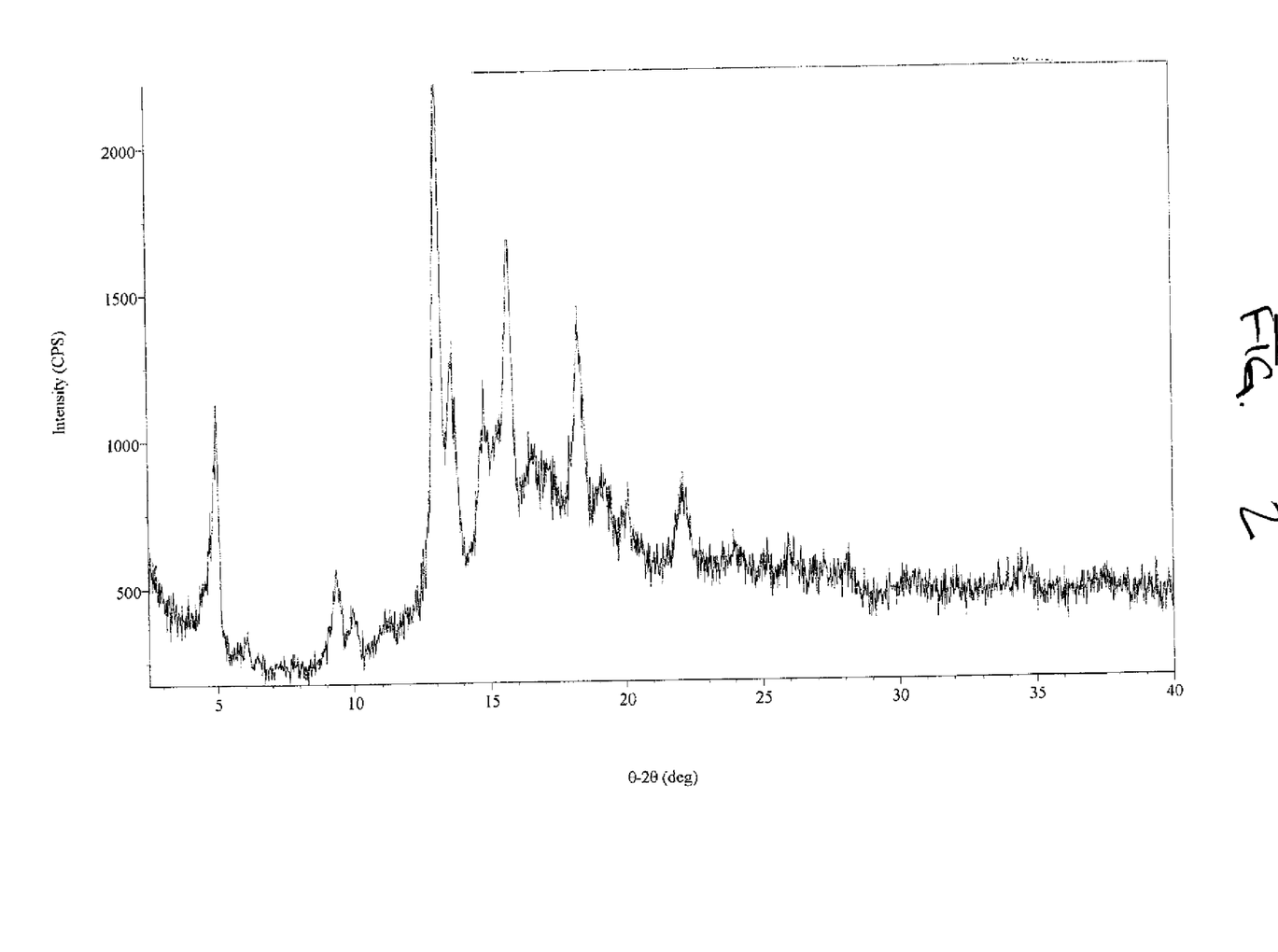
FIG. 2 is a powder x-ray diffraction scan of a polymorph of stevioside on a plot of the scattering intensity versus the scattering angle 2 θ in accordance with an embodiment of this invention.
Figure 3:
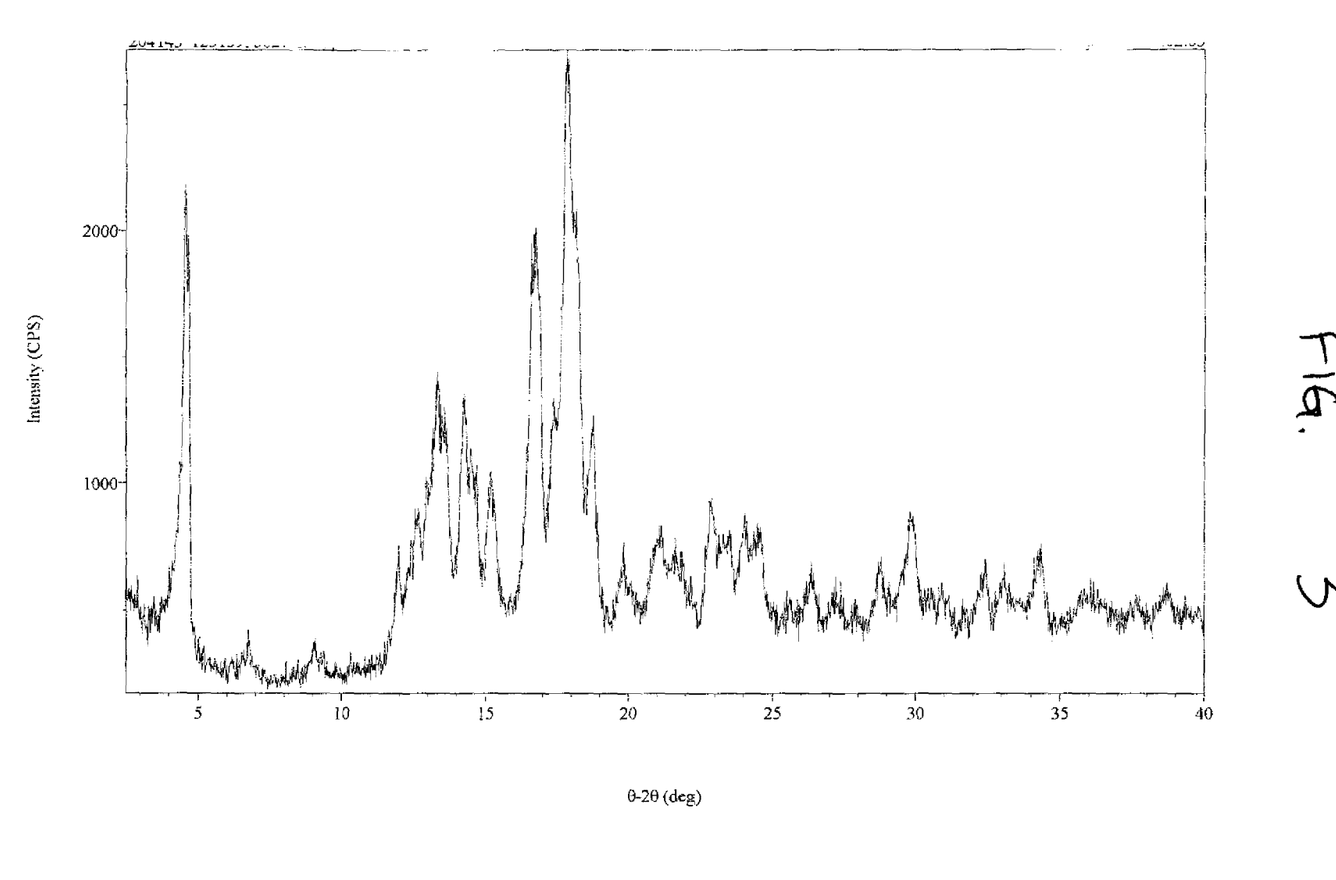
FIG. 3 is a powder x-ray diffraction scan of a polymorph of stevioside on a plot of the scattering intensity versus the scattering angle 2 θ in accordance with an embodiment of this invention.
Figure 4:
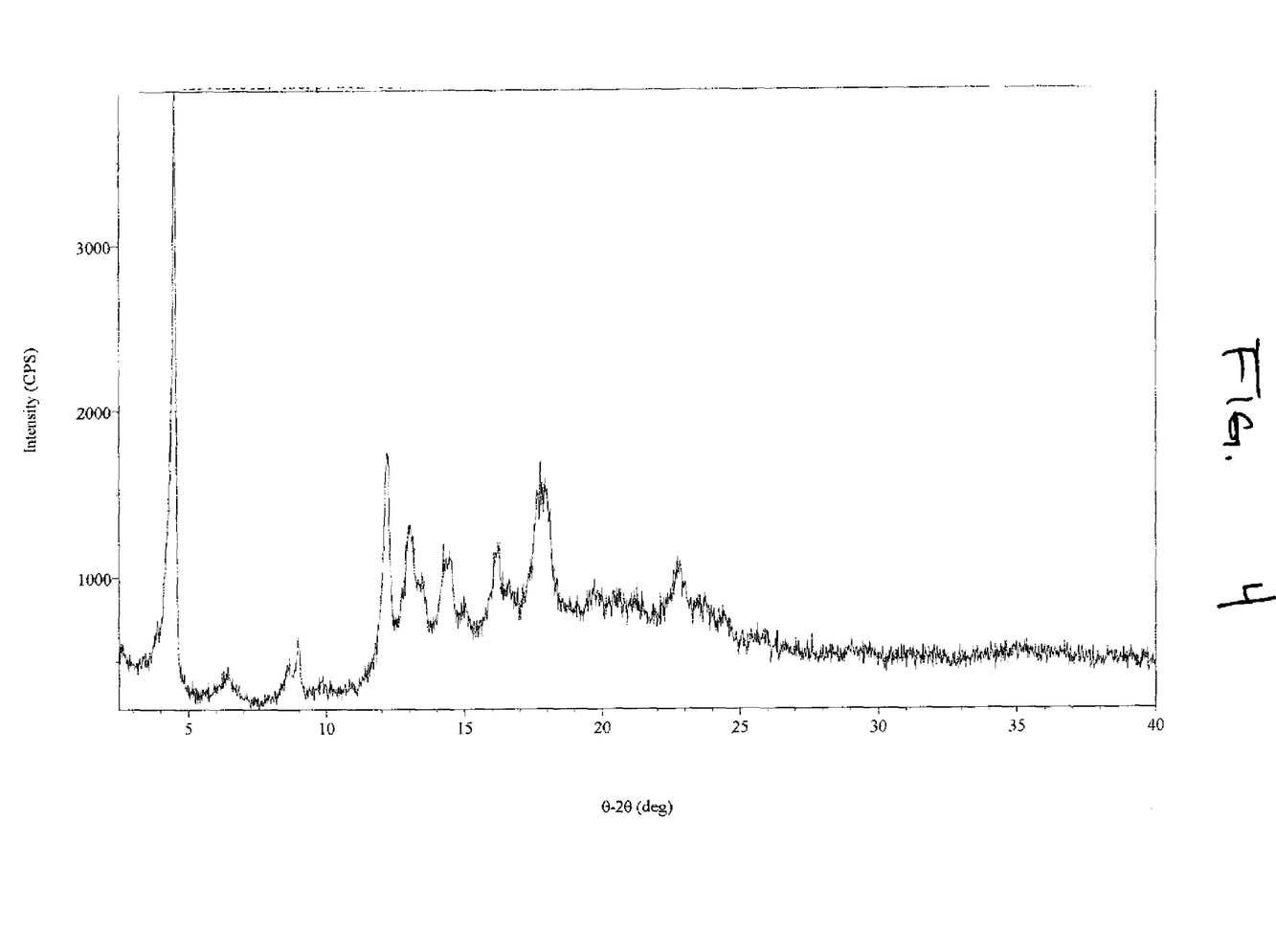
FIG. 4 is a powder x-ray diffraction scan of a polymorph of stevioside on a plot of the scattering intensity versus the scattering angle 2 θ in accordance with an embodiment of this invention.

FIG. 1 shows representative patterns for stevioside polymorphic forms prepared using the purification methods described hereinbelow using solutions comprising a methanol, ethanol, or water. In a particular embodiment a stevioside polymorph is provided having an x-ray diffraction pattern substantially similar to that of FIG. 2, 3, or 4 corresponding to Forms 1, 2A, or 2B, respectively. In another particular embodiment, a mixture of two or more stevioside polymorphs having x-ray diffraction patterns substantially similar to FIG. 2, 3, or 4 is provided.

Figure 5:
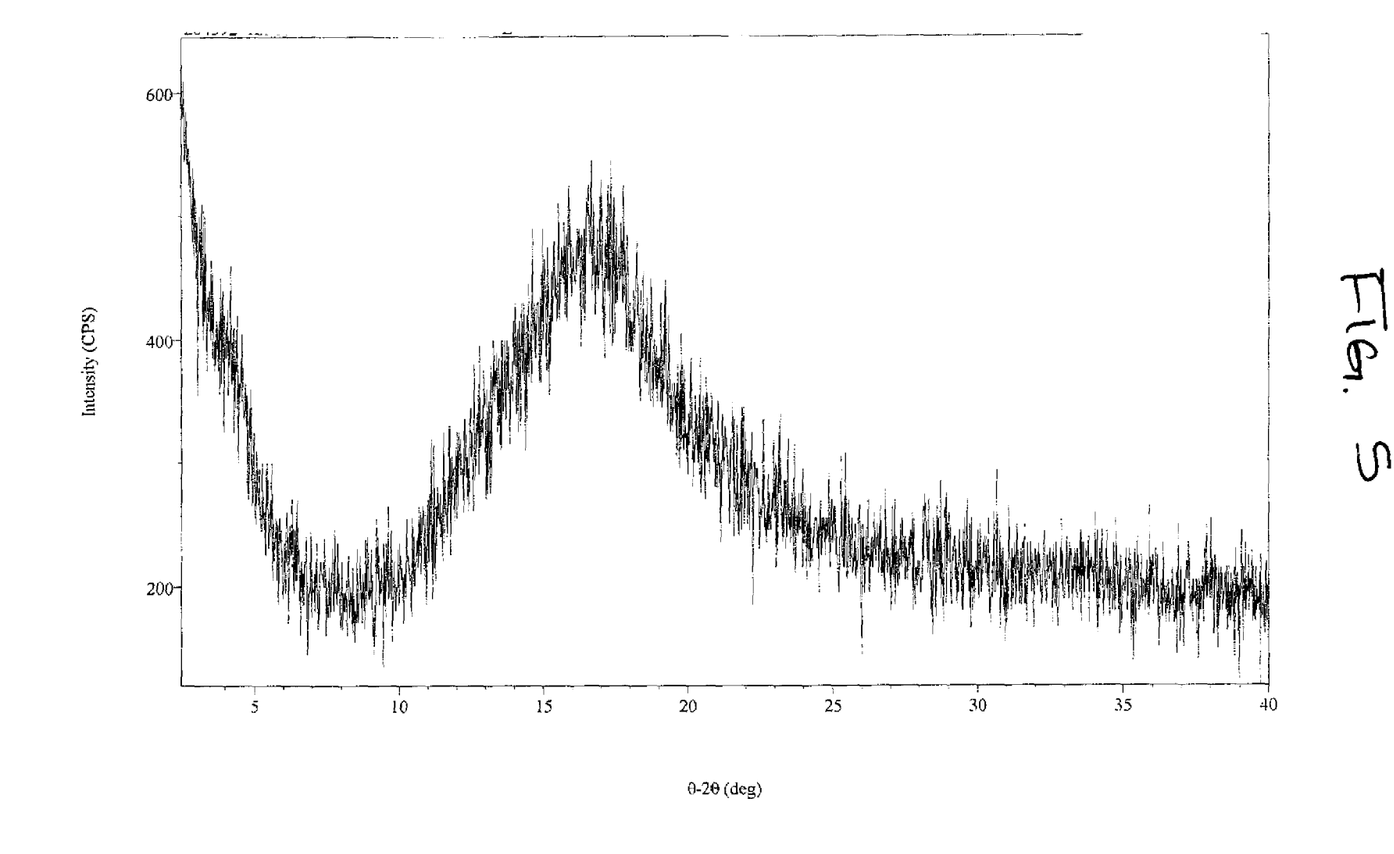
FIG. 5 is a powder x-ray diffraction scan of an amorphous form of stevioside, on a plot of the scattering intensity versus the scattering angle 2 θ in accordance with an embodiment of this invention.

In addition to the at least three polymorphic forms of stevioside, also provided herein is an amorphous form of stevioside having an x-ray diffraction pattern substantially similar to that in FIG. 5. The amorphous form of stevioside has a broad amorphous halo that identifies the composition as being amorphous. Amorphous, as used herein, describes a non-crystalline solid material. The amorphous form of stevioside is particularly desirable because of its improved rate of dissolution as compared to the polymorph forms of stevioside. It is well known to those of ordinary skill in the art that the rate of dissolution of a sweetener composition is important in the formulation of solid and liquid sweetenable compositions, non-limiting examples of which include chewing gum, baked goods, and beverages.

Also provided herein are combinations of the stevioside polymorphic and amorphous forms identified hereinabove. Accordingly, those of ordinary skill in the art should appreciate that the stevioside compositions embodied herein may be modified to obtain a desired mixture of at least one stevioside polymorphic and/or amorphous form, depending on the desired qualities of the stevioside composition (i.e., rate of dissolution, etc.). For example, in certain embodiments, a stevioside composition may comprise a particular polymorphic or amorphous form of stevioside in an amount in the range of about 1% to about 100% by weight, greater than about 25% by weight, greater than about 50% by weight, or greater than about 75% by weight. In another embodiment, a substantially pure form of a stevioside polymorphic or amorphous form is provided comprising a particular polymorphic or amorphous form in an amount greater than about 80% by weight, greater than about 85% by weight, greater than about 90% by weight, greater than about 95% by weight, or greater than about 98% by weight.

The polymorphic and amorphous forms of stevioside provided herein also may be combined with the polymorphic and/or amorphous forms of the substantially pure rebaudioside A disclosed in U.S. Provisional Application Nos. 60/805,216, filed on Jun. 19, 2006, and 60/889,318, filed on Feb. 12, 2007, to obtain a sweetener composition having desired properties (e.g., sweetness, rate of dissolution, etc.). For example, in a particular embodiment a rebaudioside A hydrate and stevioside hydrate may be combined. In another embodiment a rebaudioside A solvate may be combined with a stevioside solvate. Thus, any combination of the polymorphic and amorphous forms of rebaudioside A may be combined with any combination of the polymorphic and amorphous forms of stevioside provided herein.

Methods of Purifying Stevioside

Embodiments of the present invention also provide methods for the purification of stevioside to obtain a substantially pure stevioside or a substantially pure form of polymorphic or amorphous form of stevioside. According to certain embodiments, crude stevioside products are available commercially comprising stevioside in purities from about 40% to about 95% by weight, about 60% to about 85% by weight, or about 70% to about 85% by weight. It is envisioned that crude stevioside in its raw form as extracted from *Stevia* plants, may be purified by recrystallization in a method similar to that disclosed in U.S. Provisional Application Nos. 60/805,216, filed on Jun. 19, 2006, and 60/889,318, filed on Feb. 12, 2007, the disclosures of which are incorporated herein by reference in their entirety.

Figure 6:
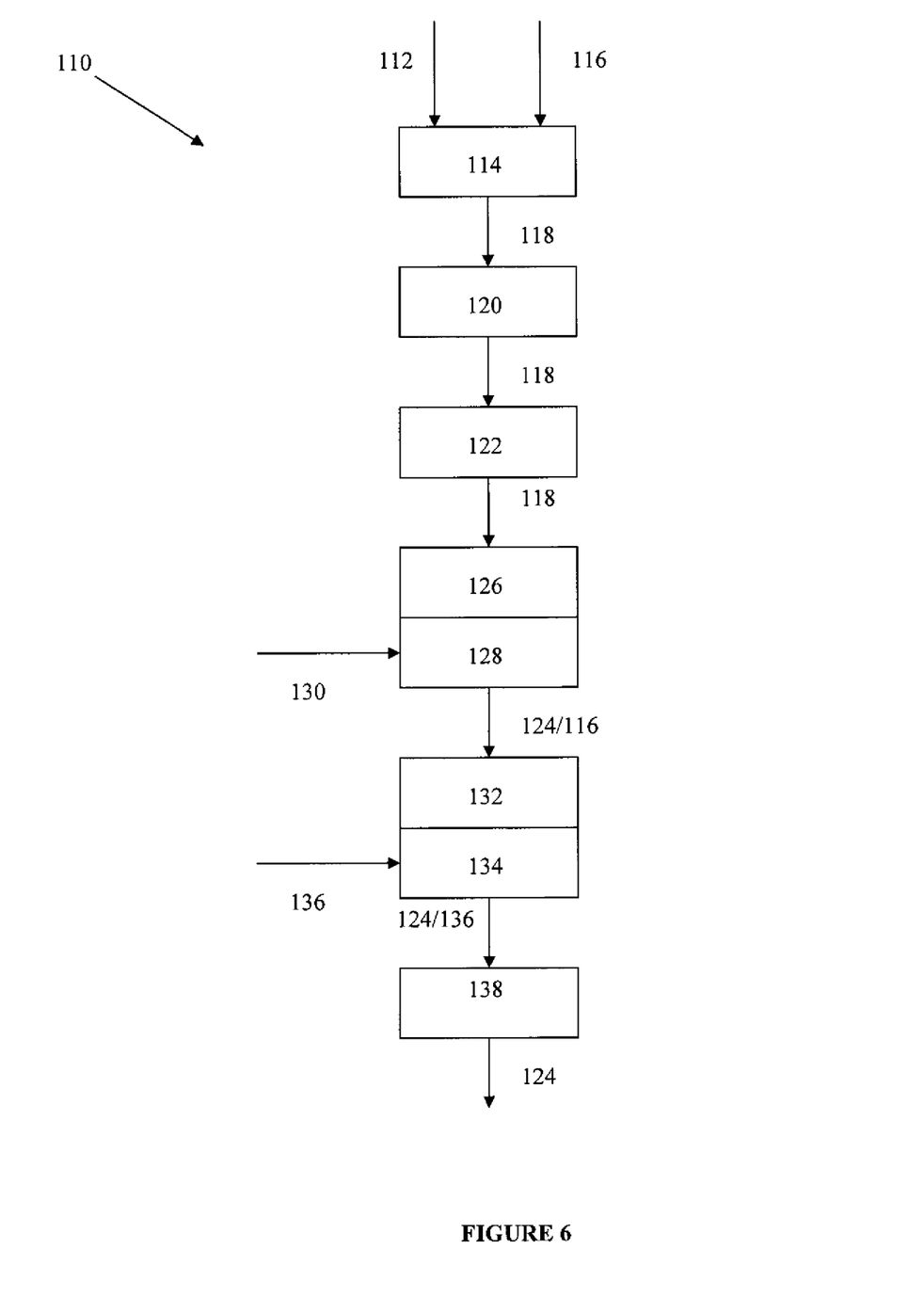
FIG. 6 is a schematic illustrating a method for purifying stevioside in accordance with an embodiment of this invention.

In a particular embodiment illustrated in FIG. 6, a method for purifying stevioside 110 comprises preparing a crude stevioside solution 118 by combining 114 a crude stevioside 112 with an aqueous organic solution or an organic solvent 116. Aqueous organic solutions 116, as used herein, comprise mixtures of at least one organic solvent and optionally water. Non-limiting examples of organic solvents include alcohol, acetone, and acetonitrile. Alcohol, as used herein, refers to any straight, branched, or cyclic; substituted or unsubstituted alkyl, alkenyl, or alkynyl groups from C1-C5 attached to at least one hydroxyl moiety. Non-limiting examples of alcohols include ethanol, methanol, isopropanol, 1-propanol, 1-butanol, 2-butanol, tert-butanol, isobutanol, and pentanol.

Those of ordinary skill in the art will appreciate that the amount of water in the aqueous organic solution 116 may be adjusted depending on the desired yield and purity. In particular embodiments, the aqueous organic solution 116 may comprise water in an amount from about 5% to about 25% by weight and at least one organic solvent, in another embodiment, the aqueous organic solution 116 may comprise water in an amount from about 5% to about 20% by weight, an amount from about 5% to about 15% by weight, an amount from about 5% to about 10% by weight, or about 8% by weight.

In particular embodiments, the crude stevioside solution 118 comprises the organic solvent or aqueous organic solution 116 and the crude stevioside 112 in a weight ratio ranging from about 10 to about 4 parts organic solvent or aqueous organic solution to about 1 part crude stevioside. In another exemplary embodiment, the crude stevioside solution 114 comprises the organic solvent or aqueous organic solution 116 and the crude stevioside 112 in a weight ratio ranging from about 5 to about 3 parts organic solvent or aqueous organic solvent to about 1 part crude stevioside.

The method for purifying stevioside 110 may further comprise heating 120 the crude stevioside solution 118 to a temperature ranging from about 20° C. to about 80° C., from about 30° C. to about 75° C., from about 40° C. to about 70° C., or any other temperature range therebetween. In another particular embodiment, the crude stevioside solution 118 is heated 120 for about 1 minute to about 8 hours.

The method for purifying stevioside 110 may further comprise cooling 122 the crude stevioside solution 118. In a particular embodiment, the crude stevioside solution 118 is cooled 122 to a temperature from about 4° C. to about 25° C. In another particular embodiment, the crude stevioside 118 solution is cooled 122 for about 0.5 hour to about 72 hours.

In a particular embodiment, a substantially pure stevioside composition 124 is crystallized 126 in the aqueous organic solution or organic solvent 116 upon cooling the crude stevioside solution 118. The substantially pure stevioside composition 124 may comprise a purity level of stevioside greater than about 80% by weight on a dry basis, greater than about 85%, greater than about 90%, greater than about 95%, greater than about 97%, greater than about 98%, or greater than about 99

The method for purifying stevioside 110 optionally may further comprise seeding 128 the crude stevioside solution 118 with substantially pure crystals of stevioside 130 in an amount sufficient to promote crystallization of the stevioside to form a substantially pure stevioside composition 124. An amount of stevioside sufficient to promote crystallization of substantially pure stevioside 124 comprises an amount from about 0.0001% to about 1% by weight of the stevioside present in the crude stevioside solution 118, and in another embodiment from about 0.01% to about 1% by weight of the stevioside present in the crude stevioside solution 118. An appropriate temperature for seeding 128 the crude stevioside solution 118 comprises a temperature in a range from about 18° C. to about 35° C.

In another embodiment, the method of purifying stevioside 110 optionally further comprises separating 132 and washing 134 the substantially pure stevioside composition 124. The substantially pure stevioside composition 124 may be separated 132 from the aqueous organic solution or organic solvent 116 by a variety of solid-liquid separation techniques that utilize centrifugal force, that include, without limitation, vertical and horizontal perforated basket centrifuge, solid bowl centrifuge, decanter centrifuge, peeler type centrifuge, pusher type centrifuge, Heinkel type centrifuge, disc stack centrifuge and cyclone separation. Additionally, separation may be enhanced by any of pressure, vacuum, and gravity filtration methods, that include, without limitation, the use of belt, drum, nutsche type, leaf, plate, Rosenmund type, sparkler type, and bag filters and filter press. Operation of the stevioside solid-liquid separation device may be continuous, semi-continuous or in batch mode. The substantially pure stevioside composition 124 also may be washed 134 on the separation device using various aqueous organic solvents 136 and mixtures thereof. The substantially pure stevioside composition 124 can be partially or totally dried on the separation device using any number of gases, including, without limitation, nitrogen and argon, to evaporate residual liquid solvent. The substantially pure stevioside composition 124 may be automatically or manually removed from the separation device using liquids, gases or mechanical means by either dissolving the solid or maintaining the solid form.

In still another exemplary embodiment, the method for purifying stevioside 110 further comprises drying 138 the substantially pure stevioside composition 124. Suitable methods for drying 138 the substantially pure stevioside composition 124 are known to those skilled in the art and include, but are not limited to, the use of a rotary vacuum dryer, fluid bed dryer, rotary tunnel dryer, plate dryer, tray dryer, Nauta type dryer, spray dryer, flash dryer, micron dryer, pan dryer, high and low speed paddle dryer and microwave dryer. In an exemplary embodiment, the substantially pure stevioside composition 124 is dried 138 using a nitrogen or argon purge to remove the residual solvent 136 at a temperature ranging from about 40° C. to about 60° C. for about 1 hour to about 100 hours.

If further purification is desired, the method of purifying stevioside 110 described herein may be repeated or the substantially pure stevioside composition 124 may be purified further using an alternative purification method, such as column chromatography (not shown).

Methods of Preparing Polymorphic and Amorphous Forms of Stevioside

It has been discovered that different polymorphic and amorphous forms of stevioside may be obtained using the purification method described hereinabove and the methods described hereinbelow. Those of ordinary skill in the art will appreciate that both the aqueous organic solution and the temperature of the purification process described herein influence the resulting polymorphic and amorphous forms that may be present in a substantially pure stevioside composition.

Figure 7:
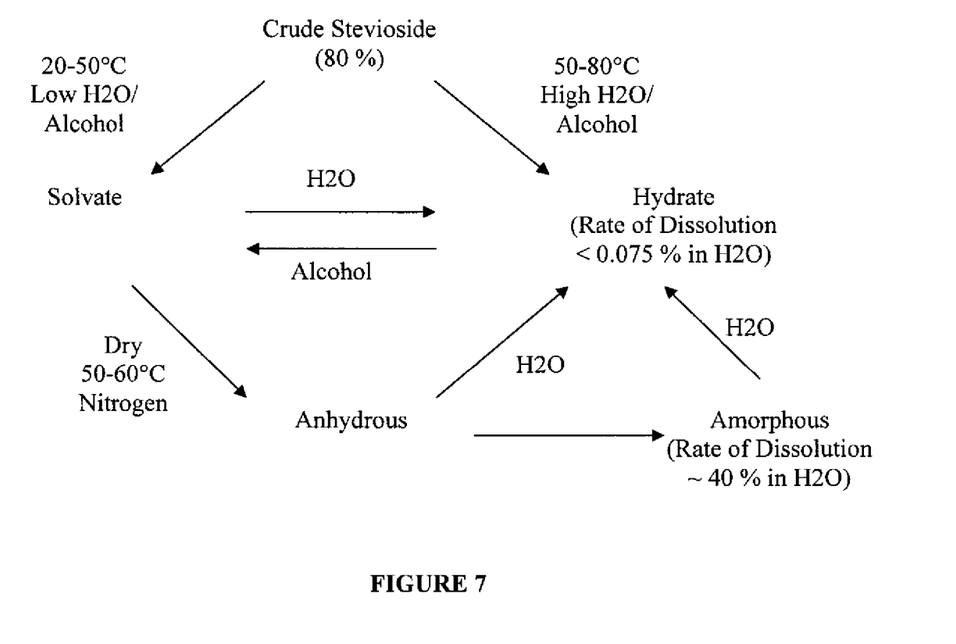
FIG. 7 is a schematic of the formation and conversion of stevioside polymorphic and amorphous forms in accordance with an embodiment of this invention.

In addition, those of ordinary skill in the art will appreciate that one may convert one polymorphic or amorphous form of stevioside to another different polymorphic or amorphous form of stevioside (FIG. 7).

For example, Form 1 can be converted to Form 2 by slurrying Form 1 in an anhydrous solvent at about room temperature for about 2 to about 16 hours or by slurrying in an anhydrous solvent at about reflux temperature for about 0.5 to about 3 hours. Form 2 can be converted to Form 1 by slurrying the polymorph in water at about room temperature for approximately 16 hours or at about reflux temperature for about 2 to about 3 hours. Form 2 can be converted to the Form 1 during the drying process; however, increasing either the drying temperature above about 70° C. or the drying time of a substantially pure Stevioside composition can result in decomposition of the Stevioside. Form 2 can be converted to Form 1 with the addition of water. An anhydrous form can be made by precipitation of Form 1 or Form 2 from an anhydrous organic solution. Form 1 and 2 can be converted to Form 3 via any of the methods described hereinbelow that will produce an amorphous form.

The amorphous form may be obtained during the initial crystallization of stevioside or directly from any individual polymorph or combination of polymorphs using methods well known to those of ordinary skill in the art. In addition, the amorphous form may be obtained from a crude stevioside composition or a substantially pure stevioside composition obtained through purification techniques well known to those of ordinary skill in the art. Non-limiting examples of methods for preparing amorphous forms of stevioside include ball milling, precipitation, lyophilization, cryogrinding, and spray-drying of a stevioside composition.

In a particular embodiment, the amorphous form can be prepared from a stevioside composition by spray-drying a solution of the stevioside composition. Briefly described, spray-drying generally requires feeding a solution of stevioside through a feed pump into a nozzle atomizer which atomizes the solution into a spray of droplets with the help of a constant flow of nitrogen/air. The moisture is evaporated from the droplets under controlled temperature conditions and air-flow conditions in the drying chamber, resulting in the formation of dry particles of amorphous stevioside. The purity of the amorphous stevioside will depend upon the purity of the solution of stevioside.

In another particular embodiment, the amorphous form can be prepared from a stevioside composition by milling non-amorphous forms of stevioside. Milling is a mechanical process that is believed to produce localized areas of energy that convert crystalline forms of stevioside to the amorphous form. Exemplary milling techniques include ball milling or air jet milling, both techniques well known to those of ordinary skill in the art. Briefly described, non-amorphous forms of stevioside are milled for a period of time and at a speed effective to form an amorphous stevioside. These parameters may be determined by those of ordinary skill in the art. Typical milling time periods may range from about 15 minutes to about 2 hours, although other time periods also may be employed.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description therein, may suggest themselves to those skilled in the art without departing from the spirit of the present invention and/or the scope of the appended claims. Unless otherwise specified, percentages (% s) are by weight.

The purity of the stevioside compositions obtained hereinbelow was determined using HPLC. Methods of performing HPLC analysis are well known to those of ordinary skill in the art. Briefly described, the HPLC analysis was performed using a ZORBAX $NH_2$ column (150×4.6 mm, 5 µm) at a temperature of 30° C. The mobile phase comprised a solution of 20% buffer and 80% acetonitrile at a flow rate of 1.5 mL/min. 12 µL of each sample was injected in duplicate and the sample was analyzed using a UV detector at 210 nm (4 nm bandwidth) with a reference of 260 nm (100 nm bandwidth). The HPLC analysis required a run time ranging from 40 to 60 min.

A buffer solution of 0.0125% acetic acid and 0.0125% ammonium acetate was prepared by dissolving 0.125 g ammonium acetate and 125 µL glacial acetic acid in one liter of water. The mobile phase was prepared by mixing the buffer solution with acetonitrile to achieve a stevioside retention time of 4.5±0.5 min. Initially, this was approximately 20% buffer (200 mL of buffer and 800 mL of acetonitrile). Increasing the amount of acetonitrile by 1 to 2% increased the retention time of stevioside by about one minute.

A diluent solution was prepared by mixing 750 mL of acetonitrile and 250 mL of the buffer solution. Stevioside standards were prepared by diluting 12.5±0.5 mg (recorded to the nearest 0.1 mg) of the Stevioside standard with 5 mL of the diluent solution to make a standard solution of approximately 2500 mg/L standard (stock A) (correcting for moisture and purity). The stevioside standard was then diluted using one mL of stock A to ten mL of diluent to produce a 250 mg/L standard (stock B), and stock standards were diluted to final concentrations ranging from 2.5 to 50 mg/L. The moisture content was measured by Karl Fischer analysis every time a standard was prepared and corrections were made based on the solvent purity according to the certificate of analysis.

The following table provides a guideline for retention times (RT) for Stevioside and other steviol glycosides. However, those of ordinary skill in the art should appreciate that the retention times may be modified as needed.

TABLE 1

HPLC Retention Guidelines

| Compound | RT (min) |
| --- | --- |
| Stevioside | 4.53 |
| Rebaudioside C | 5.21 |
| Rebaudioside F | 5.62 |
| Rebaudioside A | 7.07 |
| Rebaudioside D | 15.79 |
| Steviolbioside | 18.35 |
| Rebaudioside B | 35.83 |

Karl-Fischer analysis also was performed on the stevioside compositions obtained hereinbelow to determine the water content using a Mettler Toledo DL39 Karl Fischer titrator. Approximately 11-56 mg of sample were dissolved in approximately 3.5-3.7 g of dry Hydranal-Coulmat AD. Approximately 0.9-1.0 g of the resulting solution was placed in the KF titration vessel containing Hydranal-Coulomat AD and mixed for 10 seconds to ensure dissolution. The sample was titrated by means of a generator electrode which produces iodine by electrochemical oxidation: $2\ I^- \rightarrow I_2 + 2e$. The experiments were repeated in triplicate to ensure reproducibility.

The material properties of the three Stevioside polymorphs and the Stevioside amorphous form are summarized in the following table:

TABLE 2

Stevioside Polymorphic and Amorphous Forms

| | Form 1 Polymorph | Form 2 A Polymorph | Form 2B Polymorph | Form 4 Amorphous |
| --- | --- | --- | --- | --- |
| Rate of dissolution in H2O at 25° C. | <0.075% in 30 min | <0.6% in 2 min | 10.0% in <1.0 min | 40.0% in <1.0 min |
| Moisture content | >5% | <3% | <4% | ~3% |

Example A

Crude stevioside was obtained from commercial source. The impurities (76.8% stevioside, 8.24% rebaudioside A, 2.38% steviolbioside, 0.109% rebaudioside D, 4.133% other steviol glycosides, 0.293% rebaudioside B, 2.38% steviolbioside) were identified and quantified using HPLC on a dry basis (moisture content 3.92%).

Crude stevioside (76%, 1 g) was suspended in 30.0 mL of methanol (99%) and warmed to 45° C. with continuous stirring for 10 minutes. Water was added in a dropwise manner (~2.5 mL) until the crude material was completely dissolved and the solution was clear. The clear solution was filtered while hot and then cooled to room temperature overnight. The precipitated solid was filtered and washed with methanol (2×3×4 mL, 99%) and dried in a vacuum oven at 50° C. for 3-4 hours under reduced pressure (20 mm) to yield 0.588 g of purified Stevioside (>95% by HPLC) on a dry basis (moisture content 2.63%). XRPD results, illustrated in FIG. 3, indicate that the crystallized stevioside was a different crystalline form.

Example B

Crude stevioside (>76%, 5 g) was obtained from a commercial source and suspended in 100 mL of ethanol (99.96%) and warmed to 69° C. The stevioside dissolved within 5 minutes. The solution was boiled for another 10 minutes and allowed to cool at room temperature for two days. The crystallized stevioside was filtered and dried in a vacuum oven at 48-50° C. for 3.5 hours under reduced pressure (20 mm) to obtain a 73.00% yield of a pure crystallized stevioside (>97.0% by HPLC) on a dry basis (moisture content 3.55%). The XRPD results, illustrated in FIG. 4, indicate that the crystallized stevioside was a different crystalline form than that in Example A.

Example C

Stevioside (>97%, 2 g) obtained from Example B was dissolved in 100 mL water by stirring the solution at 44° C. for 1 minute. The solution was allowed to cool to room temperature and was left for one day. The precipitate was filtered and dried at 60° C. for 24 hours in a vacuum oven under reduced pressure (20 mm) to obtain a 95% yield of crystallized stevioside (>97.0% by HPLC) on a dry basis (moisture content 5.33%). The XRPD results, illustrated in FIG. 2, indicate that the crystallized stevioside was a different crystalline form than in Example A or B.

Example D

A concentrated solution was prepared from the crystallized stevioside obtained from Example B by dissolving 5.0 g of the crystallized stevioside in 200 mL water solution and heating to 40-50° C. until clear. The hot clear solution was spray dried with the Lab-Plant spray drier SD-04 instrument (Lab-Plant Ltd., West Yorkshire, U.K.). The solution was fed through the feed pump into the nozzle atomizer, which atomized the stevioside solution into a spray of droplets with the help of a constant flow of nitrogen/air. Moisture was evaporated from the droplets under controlled temperature conditions (about 90 to about 97° C.) and airflow conditions in the drying chamber and resulted in the formation of dry particles. This dry powder was discharged continuously from the drying chamber and was collected in a clean dried collection bottle A 98% yield of pure stevioside (>97% by HPLC) on a dry basis (moisture content 3.20%) was obtained. The XRPD results, illustrated in FIG. 5, indicate that the stevioside was an amorphous form.

While the invention has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereof.

We claim:

1. A method for purifying a polymorphic and/or amorphous form of stevioside consisting of:
   combining a crude stevioside mixture containing an extract from *Stevia* plants and an aqueous organic solvent to form a stevioside solution, the aqueous organic solvent containing water in an amount from about 5% to about 25% by weight and at least one organic solvent; and crystallizing the stevioside solution in a single crystallization step to obtain a polymorphic and/or amorphous stevioside composition containing stevioside in a purity greater than 95% by weight on a dry basis;

wherein the crude stevioside mixture contains comprises stevioside in a purity from about 60% to about 85% by weight on a dry basis; and wherein the at least one organic solvent is selected from the group consisting of acetone, acetonitrile, methanol, ethanol, 1-propanol, isopropanol, 1-butanol, 2-butanol, tert-butanol, isobutanol, and mixtures thereof.

2. The method of claim 1, wherein the crude stevioside mixture contains stevioside in a purity from about 70% to about 85% by weight.

3. The method of claim 1, wherein the at least one organic solvent is selected from the group consisting of methanol, ethanol, 1-propanol, isopropanol, 1-butanol, 2-butanol, tert-butanol, and isobutanol.

4. The method of claim 3, wherein the at least one organic solvent is ethanol.

5. The method of claim 1, wherein the organic solvent or aqueous organic solvent and the crude stevioside mixture are present in the stevioside solution in a weight ratio from about 3 to about 5 parts organic solvent or aqueous organic solvent to 1 part crude stevioside.

6. The method of claim 1, wherein the aqueous organic solvent contains water in an amount from about 10% to about 25% by weight.

7. The method of claim 1, wherein the stevioside solution in the single crystallization step is stirred or unstirred.

8. The method of claim 1, wherein the method is carried out at room temperature.

9. The method of claim 1, wherein the stevioside composition contains stevioside in a purity greater than 97% on a dry basis.

10. The method of claim 1, wherein the stevioside composition contains stevioside in a purity greater than 98% by weight on a dry basis.

11. The method of claim 1, wherein the stevioside composition contains stevioside in a purity greater than 99% by weight on a dry basis.

* * * * *